(12) United States Patent
Ostanin

(10) Patent No.: US 7,543,476 B2
(45) Date of Patent: Jun. 9, 2009

(54) RUPTURE EVENT SENSORS

(75) Inventor: Victor Petrovich Ostanin, Cambridge (GB)

(73) Assignee: Akubio Limited, Cambridge (GB)

( * ) Notice: Subject to any disclaimer, the term of this patent is extended or adjusted under 35 U.S.C. 154(b) by 98 days.

(21) Appl. No.: 10/553,471

(22) PCT Filed: Apr. 14, 2004

(86) PCT No.: PCT/GB2004/001609

§ 371 (c)(1),
(2), (4) Date: Oct. 16, 2006

(87) PCT Pub. No.: WO2004/095011

PCT Pub. Date: Nov. 4, 2004

(65) Prior Publication Data

US 2007/0062287 A1    Mar. 22, 2007

(30) Foreign Application Priority Data

Apr. 17, 2003 (GB) ................... 0308950.5
Sep. 12, 2003 (GB) ................... 0321443.4

(51) Int. Cl.
   *G01N 15/06* (2006.01)
(52) U.S. Cl. ............... 73/19.03; 73/24.03; 73/24.06; 73/31.06; 73/61.75; 73/61.71; 73/53.01; 73/579
(58) Field of Classification Search ............ None
See application file for complete search history.

(56) References Cited

U.S. PATENT DOCUMENTS 4,085,388 A * 4/1978 Gilden et al. ........ 331/107 A
4,760,351 A * 7/1988 Newell et al. ............ 331/48
4,872,765 A * 10/1989 Schodowski ............ 374/117
5,042,288 A   8/1991 Vig (Continued)

FOREIGN PATENT DOCUMENTS

DE    3618798 A1    12/1987

(Continued)

OTHER PUBLICATIONS

F. N. Dultsev et al., "Direct and Quantitative Detection of Bacteriophage by 'Hearing' Surface Detachment Using a Quartz Crystal Microbalance", Analytical Chemistry, American Chemical Society, vol. 73, No. 16, Aug. 15, 2001, pp. 3935-3939, XP-001089327.

*Primary Examiner*—Hezron Williams
*Assistant Examiner*—Rose M Miller
(74) *Attorney, Agent, or Firm*—Blank Rome LLP

(57) ABSTRACT

An apparatus for separating an analyte from a mixture or for detecting an analyte or for determining the affinity, or a property related to affinity, between binding partners includes: a) a surface having the analyte or one of the binding partners immobilized thereon, in use; b) a transducer for oscillating the surface; c) a controller connected to the transducer for varying the amplitude and/or frequency of the oscillation to cause a dissociation event; and, d) an analyzer connected to the transducer for detecting an oscillation of the transducer due to the dissociation event. The controller includes an oscillator connected in a resonant circuit with the transducer such that the transducer oscillates at two frequencies simultaneously, one of these causing the transducer to oscillate the surface and the other being supplied as an output to the analyzer.

22 Claims, 7 Drawing Sheets

U.S. PATENT DOCUMENTS

| | | | |
|---|---|---|---|
| 5,744,902 A * | 4/1998 | Vig | 310/360 |
| 6,293,136 B1 | 9/2001 | Kim | |
| 6,589,727 B1 * | 7/2003 | Klenerman et al. | 435/4 |
| 6,865,949 B2 | 3/2005 | Blakley | |
| 6,978,656 B2 | 12/2005 | Blakley | |
| 6,990,852 B2 | 1/2006 | Berndt | |
| 7,093,482 B2 | 8/2006 | Berndt | |
| 7,195,909 B2 * | 3/2007 | Klenerman et al. | 435/287.2 |
| 2003/0194697 A1 * | 10/2003 | Klenerman et al. | 435/5 |
| 2005/0132812 A1 | 6/2005 | Blakley | |

FOREIGN PATENT DOCUMENTS

| | | |
|---|---|---|
| DE | 10013795 A1 | 10/2001 |
| EP | 1 528 394 | 5/2005 |
| WO | WO 01/01121 A1 | 1/2001 |
| WO | WO 01/02857 A1 | 1/2001 |

* cited by examiner

RUPTURE EVENT SENSORS

This invention relates to apparatus for separation and detection of analytes and for measuring the affinity between analytes or binding partners using Rupture Event Scanning (REVS™). In particular, it relates to apparatus for exciting mechanical oscillations in a resonator and sensing and analysing signals produced in the resonator in response to a rupture event.

The use of a thickness shear mode resonator (TSMR) for determining the affinity between binding partners is known. WO01/02857 describes a method and apparatus using a TSMR, such as is used in a quartz crystal microbalance (QCM), for this purpose. The apparatus causes the crystal to oscillate and increases the amplitude of oscillation until the acceleration of a target molecule attached to a surface of the crystal is sufficient to overcome the attractive force between the target molecule and its binding partner. and cause the bond to be broken. When this rupture event occurs, the energy released can be detected in the form of further motional oscillations in the crystal. Such oscillations have been described as acoustic emission, but in reality constitute a complex set of oscillations of the crystal.

As described in WO01/02857, the crystal is caused to oscillate at its fundamental resonant frequency. Motional energy of the attached species is dissipated as the amplitude of the oscillation is increased, leading up to a release of significant energy at the rupture event. The electrical signal generated from the motional oscillations in the crystal is filtered near the third harmonic of the crystal driving frequency. The apparatus comprises an oscillator circuit for exciting the fundamental resonance of the crystal and a second frequency synthesizer connected to an analyser to which the filtered output from the crystal is also connected. The second frequency synthesizer operates at a frequency, $\Delta f$, higher than the third harmonic of the driving frequency such that, when it is mixed by the analyser with the third overtone output from the crystal, a signal at the difference frequency, $\Delta f$, is produced. Alternatively, the crystal may be excited near an overtone resonance of the crystal and the motional oscillations detected at the fundamental frequency.

This system has the disadvantage that an external frequency synthesizer of high precision and very low noise is required and this increases the complexity of the method and apparatus as well as rendering the apparatus heavier, larger and more expensive.

In accordance with the present invention, there is provided apparatus for separating an analyte from a mixture or for detecting an analyte or for determining the affinity, or a property related to affinity, between binding partners comprising:

a) a surface having the analyte or one of the binding partners immobilised thereon, in use;

b) a transducer for oscillating the surface;

c) a controller connected to the transducer for varying the amplitude and/or frequency of the oscillation to cause a dissociation event; and, d) an analyser connected to the transducer for detecting an oscillation of the transducer due to the dissociation event;

characterised in that the controller includes an oscillator connected in a resonant circuit with the transducer such that the transducer oscillates at two frequencies simultaneously, one of these causing the transducer to oscillate the surface and the other being supplied as an output to the analyser.

In accordance with a second aspect of the present invention, there is provided a method for separating an analyte from a mixture or for detecting an analyte or for determining the affinity, or a property related to affinity, between binding partners, the method comprising:

a) immobilising the analyte or one of the binding partners on a surface;

b) oscillating the surface;

c) varying the amplitude and/or frequency of the oscillation to cause a dissociation event; and, d) detecting an oscillation due to the dissociation event using an analyser;

characterised by oscillating the surface at two frequencies simultaneously, one of these causing the surface to oscillate and the other being supplied as an output to the analyser for use in detecting the oscillation due to the dissociation event.

Hence, the invention provides an apparatus for separating an analyte from a mixture, detecting an analyte or for determining the affinity, or a property related to affinity, between binding partners that is simpler, cheaper and more portable than the prior art.

The transducer may oscillate at any two frequencies but, in one embodiment, the frequency that is supplied as an output to the analyser is a multiple of the frequency that causes the surface to oscillate. For example, the frequency that causes the surface to oscillate is the transducer's fundamental resonant frequency and the frequency supplied as an output to the analyser is one of the transducer's overtone frequencies.

In an alternative embodiment, the frequency that causes the surface to oscillate is a multiple of the frequency that is supplied as an output to the analyser. For example, the frequency that causes the surface to oscillate is one of the transducer's overtone frequencies and the frequency supplied as an output to the analyser is the transducer's fundamental frequency.

Typically, the oscillation of the transducer due to the dissociation event is at a range of frequencies located around at least one of the transducer's resonant frequencies.

The apparatus may be used with a variety of analytes and binding partners but typically, the immobilised analyte or binding partner is a metal (for example, gold, silver, copper or aluminium), a polymer (for example, polystyrene, poly vinyl alcohol or a polysaccharide), a dendrimer, a self-assembled monolayer, a peptide, a protein, an antibody, an antigen, an enzyme, enzyme inhibitor, a biologically active molecule, a drug, a polynucleotide (for example DNA) or a peptide-polynucleotide (for example PNA). Alternatively, the immobilised analyte or binding partner may be a biological entity such as a cell, a bacterium, a virus, a prion, an amyloid, a proteinaceous aggregate or a phage.

The apparatus may be used with only one analyte or pair of binding partners, one of which is immobilised on the surface. However, the apparatus may be used with several analytes or binding partners simultaneously. Thus, typically, different analytes or binding partners are immobilised at different positions on the surface.

Normally, the dissociation event is detected as a motional oscillation. This motional oscillation may produce an electrical signal in the transducer.

Typically, the transducer is an acoustic wave device, and in this case it may be a piezoelectric transducer, such as a quartz crystal, as used in a microbalance, or a surface acoustic wave device. A suitable piezoelectric transducer may comprise zinc oxide, a piezoelectric polymer (for example polyvinylidene fluoride), a piezo-electric semiconductor (for example Gallium Arsenide) or a piezo-ceramic (for example lithium tantalate). Alternatively, the transducer may be an electromagnetic device.

When the transducer is a piezoelectric transducer, the oscillator may be a dual mode crystal resonator.

In a preferred embodiment, the oscillator comprises two bandpass filters, each having its input connected to the transducer and its output connected to a respective amplifier, the outputs of which are combined by a power adder and supplied to the transducer, the centre frequencies of the bandpass filters corresponding to the two oscillating frequencies of the transducer.

Typically, the analyser comprises a radiofrequency detector and a digitiser.

An example of the invention will now be described with reference to the accompanying drawings, in which:

FIG. 1 shows, schematically, one embodiment of the invention;

FIGS. 2 and 3 each show, schematically, a first implementation of the embodiment of FIG. 1;

Figure 1:
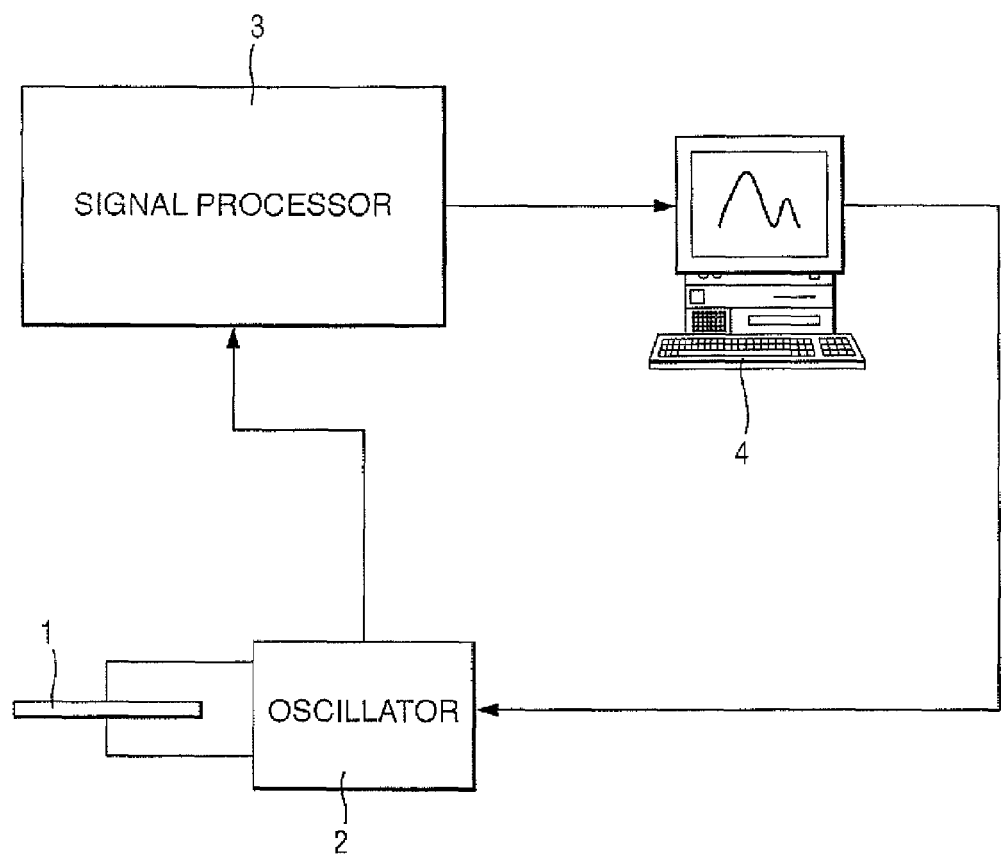

More specifically, FIG. 1 shows a thickness shear mode resonant sensor such as a quartz crystal 1 connected in a resonant circuit with oscillator 2. Oscillator 2 is a dual frequency crystal oscillator and excites two resonant oscillations of crystal 1, namely the fundamental and its third overtone.

An output from oscillator 2 is connected to signal processor 3. The output from signal processor 3 is connected to computer 4 which analyses and displays the results. Computer 4 also has a control output connected to oscillator 2 for varying the amplitude of oscillation.

In use, one of a pair of binding partners for which it is wished to determine the affinity is immobilised on the surface of the crystal 1, which is caused to oscillate at its fundamental and third overtone frequencies by oscillator 2. The magnitude of the third overtone oscillation of crystal 1 is much lower in magnitude than that of the fundamental oscillation such that it is comparable in amplitude with the signal produced when a rupture event occurs.

It is important to note that the energy released by the rupture event has been found to contain many frequency components. In particular these can be found in bandwidths, which include a harmonic of the driving frequency, and/or a resonant overtone frequency of the crystal. For the third harmonic and overtone, this bandwidth may be in the region of 200 kHz, but will vary depending on the harmonic used, and the properties of the crystal. It is not easy to detect the energy release by measuring the signal from the transducer exactly at the third harmonic of the driving signal because the driving signal applied to the transducer also causes oscillations of the transducer at its harmonics, due to the non-linear response of the transducer. These harmonic oscillations have a very narrow bandwidth, but in intensity mask the oscillations induced at close frequencies by the rupture event. The detection frequency is therefore best offset from the third harmonic of the fundamental resonance frequency (i.e. it is selected to be at a frequency, $\Delta f$ above or below the third harmonic), and the bandwidth of the detection system is chosen following experimental evaluation to maximise the signal to noise ratio. For example, an offset of 70-80 kHz from the third overtone resonance of the crystal with a bandwidth of up to 20 kHz has been found to give a good signal to noise ratio. Those skilled in the art will recognise that many variations are possible.

Computer 4 provides a control signal to oscillator 2 for varying the amplitude of oscillation of crystal 1. The amplitude of oscillation is increased, thereby increasing the acceleration of a binding partner immobilised on the surface of crystal 1 until the attractive force between the immobilised binding partner and another binding partner attached to it is overcome. When this occurs, the binding partners separate from each other, and this rupture event is detected by crystal 1 which produces an electrical signal in response to the associated motional oscillations.

Alternatively, an analyte may be immobilised on the surface of the crystal 1. The amplitude of oscillation is again increased until the attractive force between the analyte and the surface is overcome. The rupture event is detected as already described.

In an alternative embodiment, computer 4 varies the frequency of the driving oscillation of oscillator 2, since variation of the oscillation frequency can also be used to control the acceleration of crystal 1.

The energy released by the rupture event causes crystal 1 to oscillate, particularly near its resonant frequencies. This typically provides a signal centred around the third resonance overtone. Signals at other frequencies are also produced. The signal centred around the third overtone is isolated by signal processor 3 and displayed, after suitable analysis, on computer 4.

Figure 2:
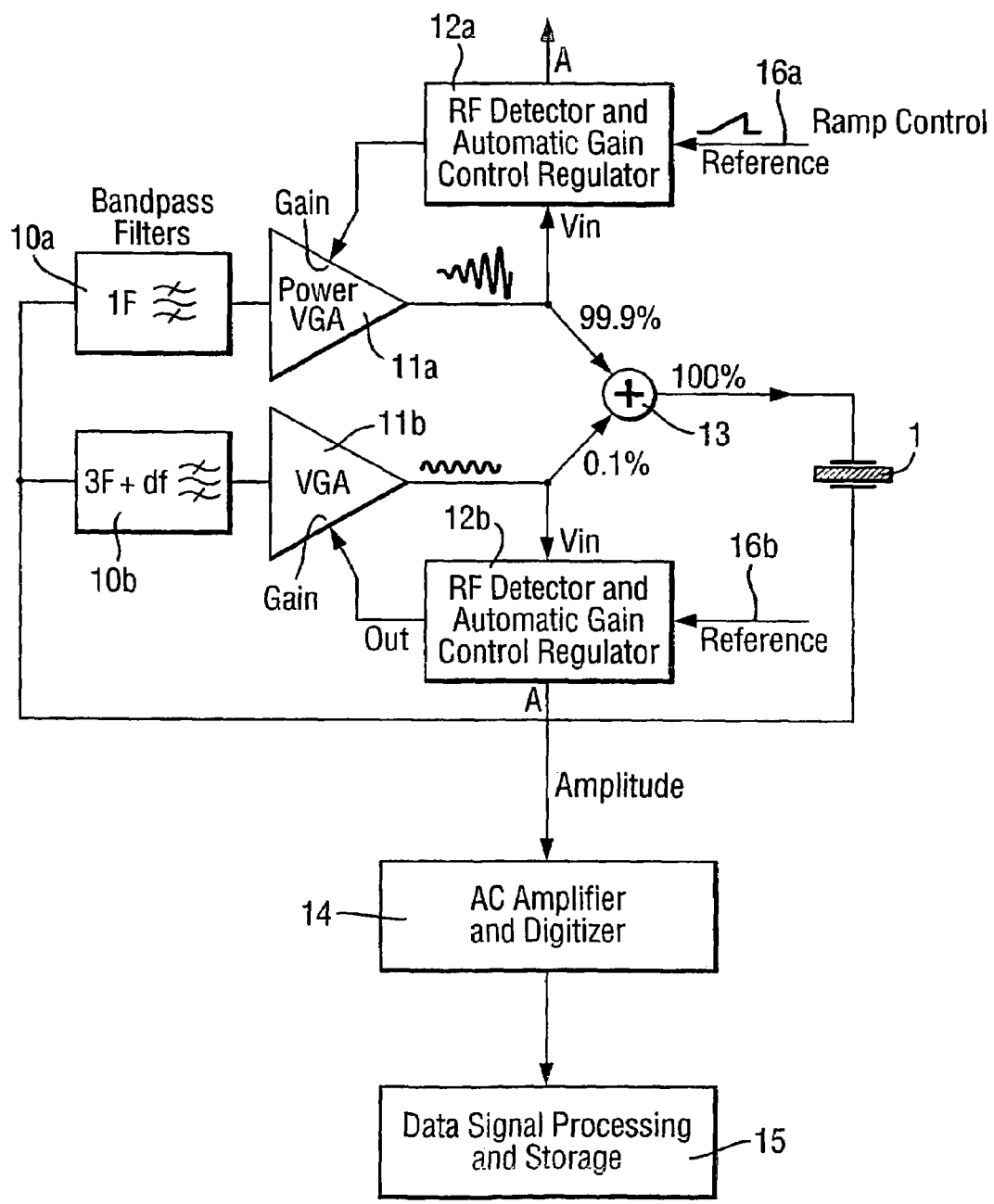

A first implementation of the embodiment described with reference to FIG. 1 is shown in FIG. 2. In this, oscillator 2 comprises bandpass filters 10a, 10b, variable gain amplifiers 11a, 11b and power adder 13. As such, bandpass filters 10a, 10b, variable gain amplifiers 11a, 11b, power adder 13 and crystal 1 form a resonant loop. Bandpass filter 10a has a centre frequency at the fundamental frequency of crystal 1 whilst bandpass filter 10b has a centre frequency at $\Delta f$ above the third harmonic of the fundamental frequency. Variable gain amplifier 11a amplifies the signal from bandpass filter 10a whilst variable gain amplifier 11b amplifies the signal from bandpass filter 10b. The outputs from variable gain amplifiers 11a, 11b are added together by power adder 13, the output of which is connected to crystal 1.

Figure 6:
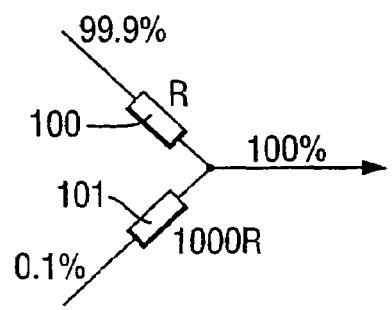
FIG. 6 shows an example of a power adder for use in the first to third implementations.

Power adder 13 combines the signals from variable gain amplifiers 11a, 11b in such a way that the signal from variable gain amplifier 11a, which is at the fundamental frequency of crystal 1, forms the majority (typically 99.9%) of the output of power adder 13 and the minority part of the output signal from power adder 13 (typically 0.1%) is formed from the output of variable gain amplifier 11b. A suitable power adder is shown in.FIG. 6. This comprises two resistors 100,101. The value of resistor 101 is typically significantly higher than that of resistor 100. In this example, resistor. 101 has a value 1000 times greater than that of resistor 100 such that the signal at their junction comprises 99.9% of the signal supplying resistor 100 and 0.1% of the signal supplying resistor 101. In this way, crystal 1 oscillates at both its fundamental frequency and at a frequency $\Delta f$ above the third harmonic. The gains of variable gain amplifiers 11a, 11b are controlled by radio frequency (RF) detectors and automatic gain control. (AGC) regulators 12a, 12b in response to reference inputs 16a, 16b. In this way, the gains of variable gain amplifiers 11a, 11b and hence, the magnitude of oscillation of crystal 1 at each frequency of oscillation can be independently controlled. The gain of amplifier 11a is then increased until such time as a rupture event occurs.

When a rupture event occurs the energy released causes an additional oscillation of crystal 1 and the rupture event signal that is produced is filtered by bandpass filters 10a, 10b. The output of variable gain amplifier 11b is connected to RF detector and AGC regulator 16b which is used to detect that portion of the rupture event signal that was within the pass band of bandpass filter 10b. This band pass can be chosen to select the range of frequencies produced by the rupture event and to be detected by detector 12b.

Figure 7:
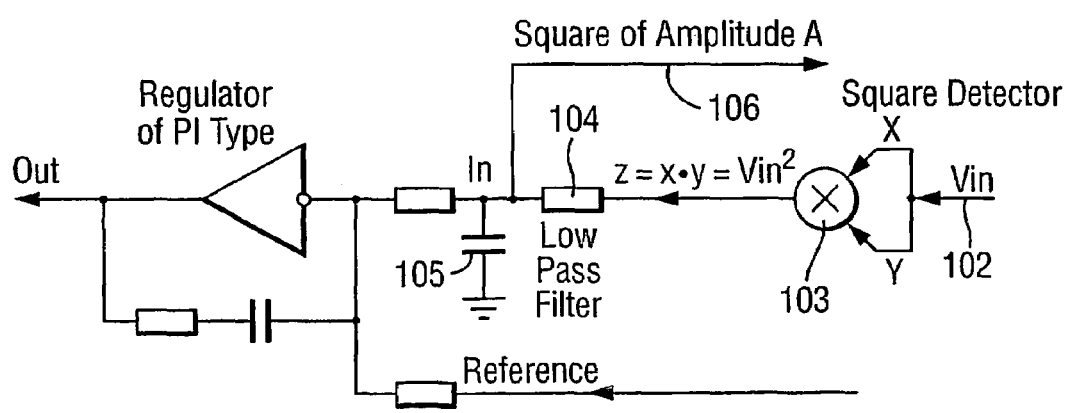
FIG. 7 shows an example of a radiofrequency detector and AGC regulator.

An example of a suitable circuit for use as RF detectors and AGC regulators 12a, 12b is shown in FIG. 7. This shows that the RF detector firstly squares an input signal 102 using multiplier 103 and then low pass filters the resulting signal using resistor 104 and capacitor 105 to produce an output signal 106, which is proportional to the power of the input. The proportional integral regulator produces a time varying output which regulates the gain of amplifiers 11a and 11b.

The squared output signal from RF detector and AGC regulator 16b includes products of all frequency components within the bandpass of filter 10b, and is time varying with components at many frequencies. It is supplied to AC amplifier and analogue-to-digital converter 14 which samples this signal at a high frequency, and supplies a digital version of its input signal to signal processing and storage device 15. This provides buffering and reduces the high data rate input to a data point set that can be analysed on a PC. Together, RF detectors and AGC regulators 12a, 12b, AC amplifier and analogue-to-digital converter 14 and signal processing and storage device 15 perform the role of signal processor 3 and computer 4.

Figure 3:
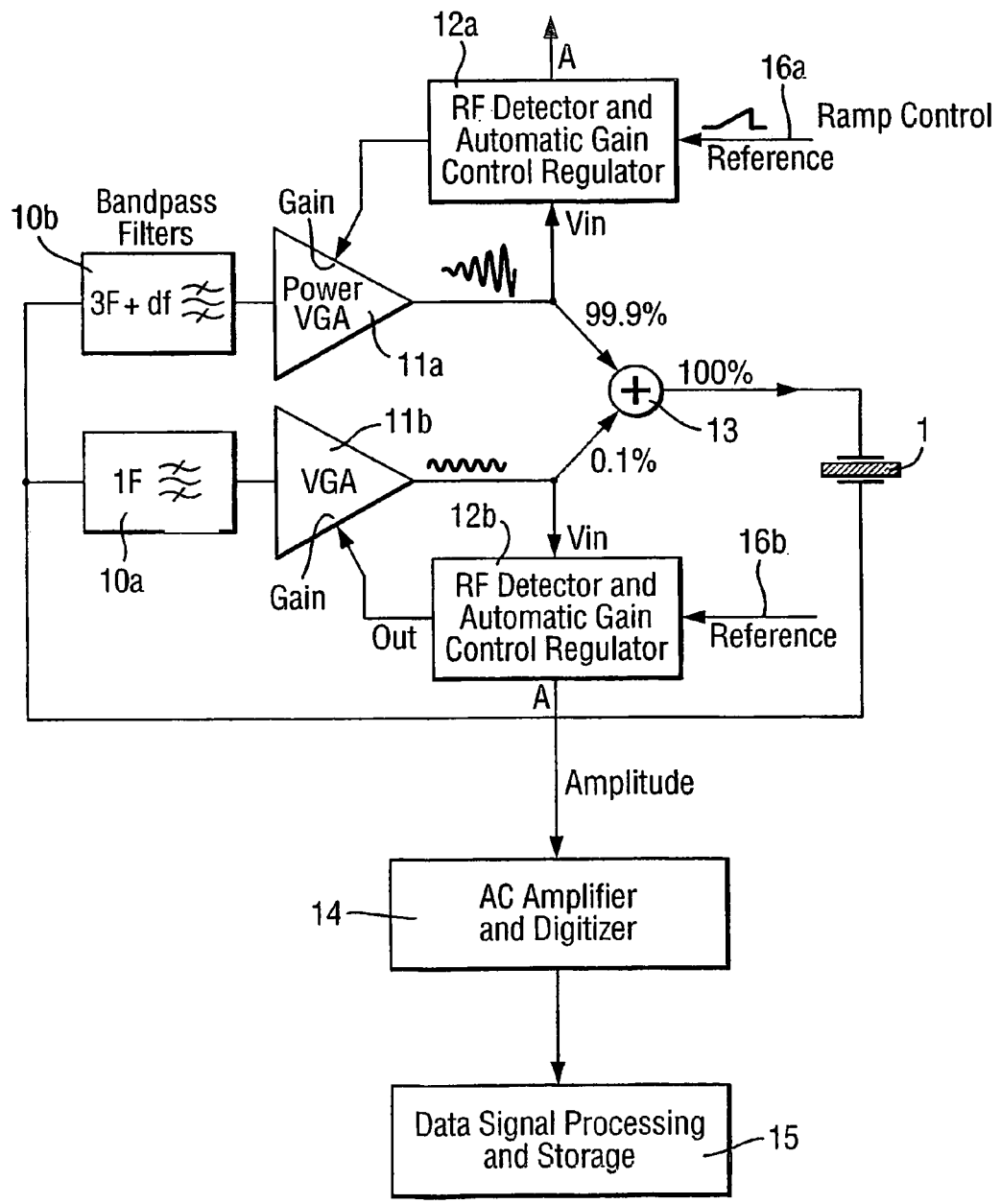

A variant of the implementation of FIG. 2 is shown in FIG. 3 in which the positions of bandpass filters 10a and 10b have been swapped. The driving signal to crystal 1 is at the third overtone resonance of the crystal which is separated from the third harmonic of the driving frequency by the frequency difference Δf. The rupture event signal is detected near the fundamental frequency of crystal 1.

The implementation shown in FIG. 3 has the advantage that the excitation of the crystal 1 at an overtone resonance does not induce subharmonics at the fundamental frequency. In contrast, excitation at the fundamental induces oscillations at overtone frequencies through non-linearities in the transducer response. It is thus easier to resolve the motional oscillation frequencies near the fundamental whilst exciting the crystal 1 at an overtone frequency than it is to resolve them at an overtone frequency whilst exciting the crystal 1 at the fundamental.

Figure 4:
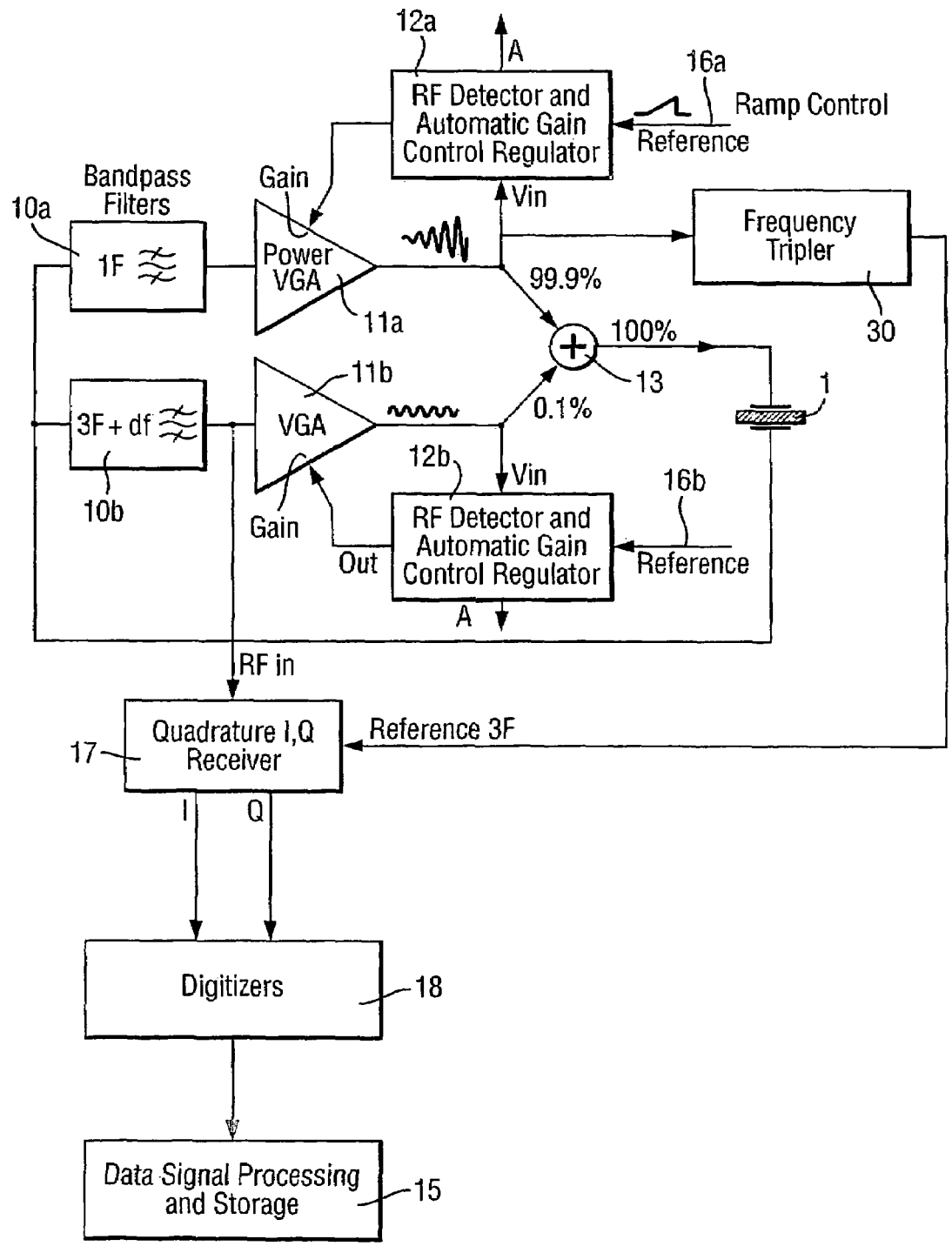
FIG. 4 shows, schematically, a second implementation of the embodiment of FIG. 1.

FIG. 4 shows a second implementation of the invention which differs from the first implementation in that the RF detectors and AGC regulators 12a, 12b are used only to control the gain of variable gain amplifiers 11a, 11b and the AC amplifier and analogue-to-digital converter 14 is replaced by quadrature receiver 17 and analogue-to-digital converters 18.

Quadrature receiver 17 is supplied with the rupture event signal from bandpass filter 10b and a signal from frequency tripler 30 which is connected to the output of variable gain amplifier 11a and hence provides a signal at the third harmonic of the drive frequency. The quadrature receiver 17 produces two down converted output signals which are in-phase and in-quadrature components having a frequency that is the difference in frequency between the two inputs. If a rupture event occurs, it will produce quick modulation of the amplitude and phase of the frequencies passed by bandpass filter 10b which will then be transformed into time varying changes in the in-phase and in-quadrature amplitudes of the down converted signal output by quadrature receiver 17.

The in-phase and in-quadrature carriers. are digitised by analogue-to-digital converters 18 and then these digital signals are supplied to signal processing and storage device 15 as before. In this implementation, RF detectors and AGC regulators 12a, 12b, quadrature receiver 17, analogue-to-digital converters 18 , frequency tripler 30 and signal processing and storage device 15 perform the role of signal processor 3 and computer 4.

Figure 5:
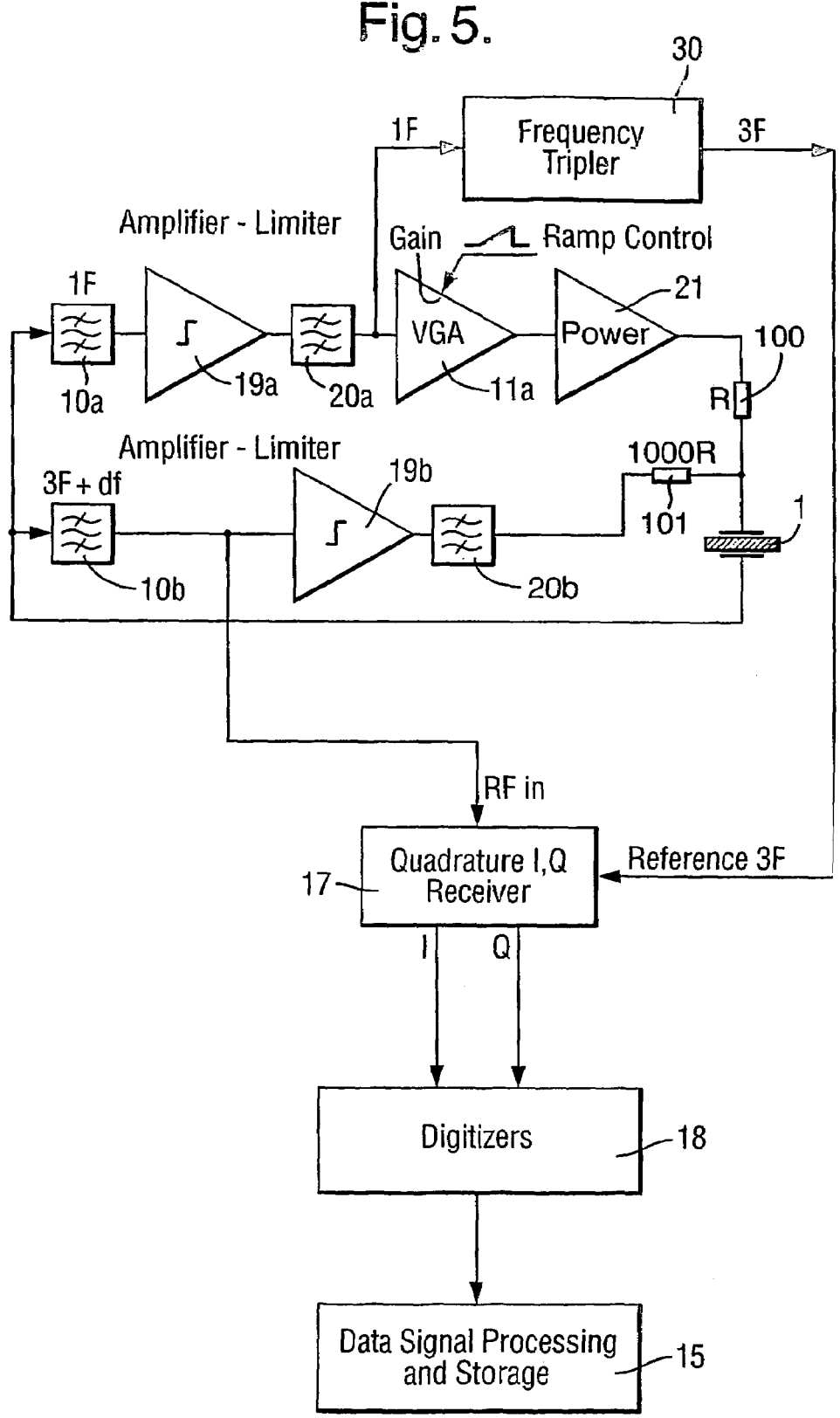
FIG. 5 shows, schematically, a third implementation of the embodiment of FIG. 1.

In the third implementation, shown in FIG. 5, variable gain amplifier 11b is replaced by limiting amplifier 19b which is connected to bandpass filter 20b. Similarly, limiting amplifier 19a and bandpass filter 20a are connected between the output of bandpass filter 10a and variable gain amplifier 11a. The limiting amplifiers 19a, 19b have very high gains in the linear range and saturate at fixed positive and negative values of input voltage. This produces an output that is practically a square wave of fixed amplitude. Limiting amplifiers 19a and 19b thus control the amplitude of the signals instead of the feedback loops through RP detectors and AGC regulators 12a and 12b. Variable gain amplifier 11b as shown in FIGS. 2, 3 and 4 is therefore not required. Limiting amplifiers are available as packages in integrated circuits and provide advantages in terms of cost.

Band pass filters 20a and 20b provide rejection of all but the fundamental and the third overtone frequency respectively, and the signal is a high quality sinusoid of fixed amplitude. These filters must be of a very high quality as they are required to attenuate the third harmonic to a level significantly lower than the level of the REVS signal. Thus, if the ratio of the signal levels in the two branches of the power adder is 1000, the attenuation must be at least 100,000 at the third harmonic. In an alternative arrangement filter 20a can be placed after power amplifier 21 to eliminate any harmonics arising in power amplifier 21.

In a further example of this type, it is also possible to dispose of frequency tripler 30, and use the third overtone signal directly as the reference to the quadrature receiver,as this is the dominant oscillation frequency.

Figure 8:
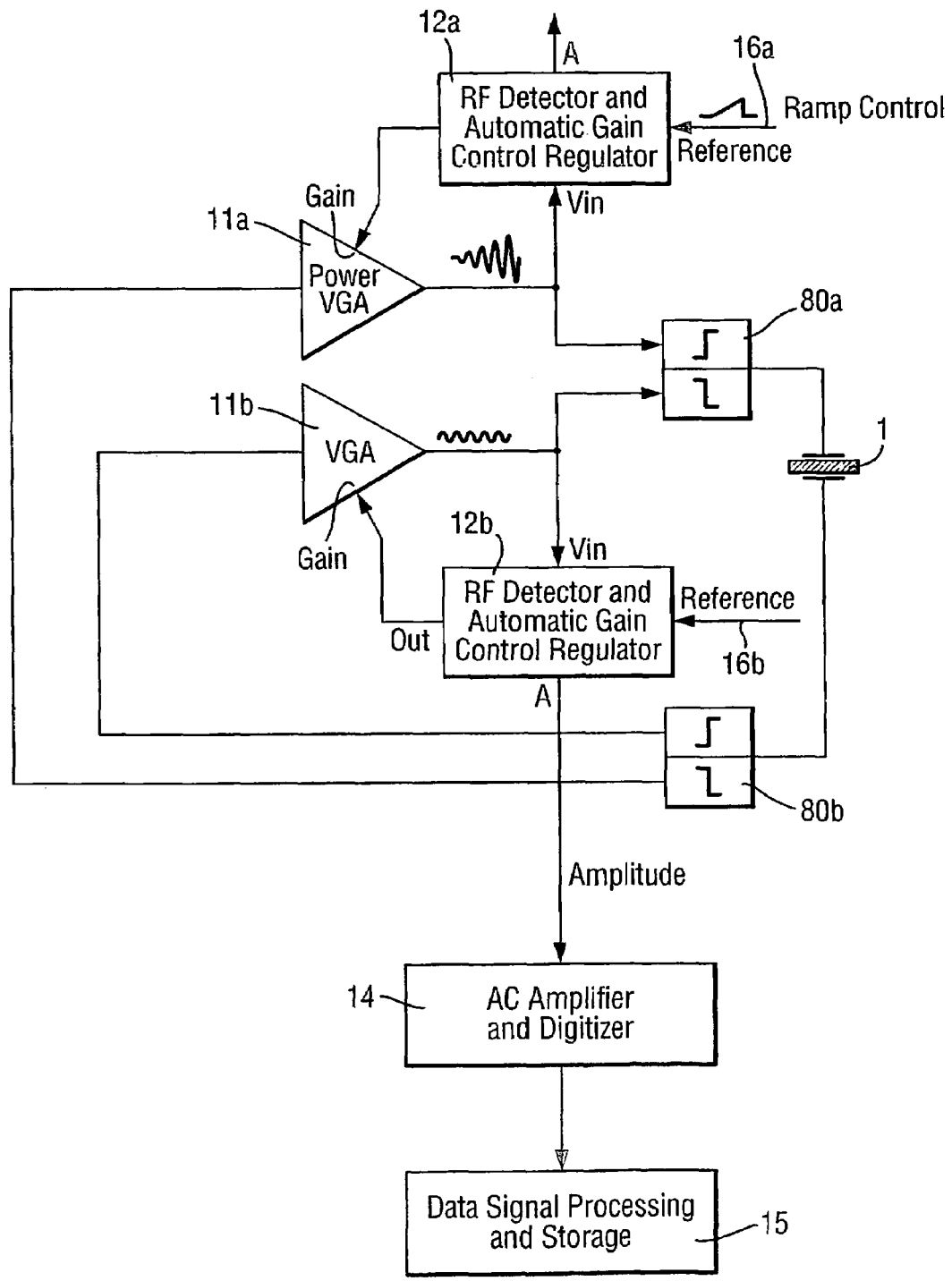
FIG. 8 shows, schematically, a fourth implementation of the embodiment of FIG. 1.

Another way of achieving self oscillation at two frequencies simultaneously uses diplexers 80a, 80b as shown in FIG. 8. These diplexers 80a, 80b combine the function of the bandpass filters and power adder shown in the earlier figures. Use of diplexers 80a, 80b has the advantage that independent and continuous control of the power levels supplied to the crystal at the fundamental and third overtone frequencies can be achieved. Thus, the amplitude of oscillation at the detection frequency can be adjusted to an appropriate level to optimise the signal to, noise ratio. Either the fundamental frequency or third overtone+Δf signal can be used interchangeably as the drive signal with the other frequency being used for detection. With the use of high isolation amplifiers (or variable attenuators) any loop can be inactivated and appear transparent to the other. Thus any number of frequencies can be provided for in the apparatus, and only those required activated. To increase oscillation stability and in order to remove any possible spurious modes a narrow band pass filter could be inserted directly after the outputs of each amplifier.

The invention claimed is:

1. Apparatus for separating an analyte from a mixture or for detecting an analyte or for determining the affinity, or a property related to affinity, between binding partners comprising:
   a) a surface having the analyte or one of the binding partners immobilised thereon, in use;
   b) a transducer for oscillating the surface;
   c) a controller connected to the transducer for varying the amplitude, frequency, or amplitude and frequency of the oscillation to cause a dissociation event; and, d) an analyser connected to the transducer for detecting an oscillation of the transducer due to the dissociation event;

characterised in that the controller includes an oscillator connected in a resonant circuit with the transducer such that the transducer oscillates at first and second frequencies simultaneously, the second frequency being supplied as an output to the analyser.

2. Apparatus according to claim 1, wherein the second frequency that is supplied as an output to the analyser is a multiple of the first frequency.

3. Apparatus according to claim 2, wherein the first frequency is the transducer's fundamental resonant frequency and the second frequency supplied as an output to the analyser is one of the transducer's overtone frequencies.

4. Apparatus according to claim 1, wherein the first frequency is a multiple of the second frequency that is supplied as an output to the analyser.

5. Apparatus according to claim 4, wherein the first frequency is one of the transducer's overtone frequencies and the second frequency supplied as an output to the analyser is the transducer's fundamental frequency.

6. Apparatus according to claim 1, wherein the oscillation of the transducer due to the dissociation event is at a range of frequencies located around at least one of the transducer's resonant frequencies.

7. Apparatus according to claim 1, wherein the immobilised analyte or binding partner is a metal, a polymer, a dendrimer, a self-assembled monolayer, a peptide, a protein, an antibody, an antigen, an enzyme, an enzyme inhibitor, a biologically active molecule, a drug, a polynucleotide or a peptide polynucleotide.

8. Apparatus according to claim 1, wherein the immobilised analyte or binding partner is a cell, a bacterium, a virus, a prion, an amyloid, a proteinaceous aggregate or a phage.

9. Apparatus according to claim 1, wherein the dissociation event is detected as a motional oscillation.

10. Apparatus according to claim 1, wherein the transducer is a piezoelectric transducer.

11. Apparatus according to claim 10, wherein the transducer is a quartz crystal microbalance.

12. Apparatus according to claim 10, wherein the transducer comprises zinc oxide, a piezoelectric polymer or a piezo-ceramic.

13. Apparatus according to claim 10, wherein the oscillator is a dual frequency crystal oscillator.

14. Apparatus according to claim 1, wherein the oscillator comprises two bandpass filters, each having its input connected to the transducer and its output connected to a respective amplifier, the outputs of which are combined by a power adder and supplied to the transducer, the centre frequencies of the bandpass filters corresponding to the two oscillating frequencies of the transducer.

15. Apparatus according to claim 1, wherein the analyser comprises a radiofrequency detector and a digitiser.

16. A method for separating an analyte from a mixture or for detecting an analyte or for determining the affinity, or a property related to affinity, between binding partners, the method comprising:
   a) immobilising the analyte or one of the binding partners on a surface;
   b) oscillating the surface;
   c) varying the amplitude, frequency, or amplitude and frequency of the oscillation to cause a dissociation event; and,
   d) detecting an oscillation due to the dissociation event using an analyser;

characterised by oscillating the surface at first and second frequencies simultaneously, the second frequency being supplied as an output to the analyser for use in detecting the oscillation due to the dissociation event.

17. A method according to claim 16, wherein the surface is oscillated using a transducer and the second frequency that is supplied as an output to the analyser is a multiple of the first frequency.

18. A method according to claim 17, wherein the first frequency is the transducer's fundamental resonant frequency and the second frequency supplied as an output to the analyser is one of the transducer's overtone frequencies.

19. A method according to claim 16, wherein the surface is oscillated using a transducer, and wherein the first frequency is a multiple of the second frequency that is supplied as an output to the analyser.

20. A method according to claim 19, wherein the first frequency is one of the transducer's overtone frequencies and the second frequency supplied as an output to the analyser is the transducer's fundamental frequency.

21. A method according to any claim 16, wherein the surface is oscillated using a transducer, and wherein the oscillation due to the dissociation event is at a range of frequencies located around at least one of the transducer's resonant frequencies.

22. A method according to claim 16, further comprising detecting the dissociation event as a motional oscillation.

* * * * *